United States Patent [19]

Clemente et al.

[11] 4,448,774
[45] May 15, 1984

[54] STEROID FORMULATION

[75] Inventors: Emmett Clemente, Manchester, Mass.; Ho-Leung Fung, Getzville, N.Y.; Denise Brousseau, Andover, Mass.

[73] Assignee: Fisons Corporation, Bedford, Mass.

[21] Appl. No.: 452,294

[22] Filed: Dec. 22, 1982

[51] Int. Cl.$^3$ .................... C07J 7/00; A61K 31/56
[52] U.S. Cl. ........................................ 424/243
[58] Field of Search ............... 260/397.45; 424/238, 424/243

[56] References Cited

U.S. PATENT DOCUMENTS 3,980,778  9/1976  Ayer et al. .................... 424/243
4,302,452 11/1981  Pittman, Jr. .................... 424/243
4,344,940  8/1982  Chow et al. .................... 424/238

Primary Examiner—Elbert L. Roberts
Attorney, Agent, or Firm—Richard P. Crowley

[57] ABSTRACT

There is described an aqueous pharmaceutical solution comprising a steroid selected from prednisolone, prednisolone sodium phosphate, prednisone and methyl prednisolone, the steroid being present at a concentration of at least 0.3 mg/ml., the pH of the formulation between 5 and 8 and the formulation containing a pharmaceutically acceptable preservative, a pharmaceutically acceptable chelating agent, and being substantially free of ethanol.

There is also described a method of treatment of a variety of conditions, particularly in children, using the solution.

20 Claims, No Drawings

STEROID FORMULATION

BACKGROUND OF THE INVENTION

This invention relates to a novel steroid formulation.

It has for many years been known to administer various steroids by a variety of routes including the oral route. To this end a wide variety of oral formulations have been suggested, but in practice the formulation most commonly used is a tablet, which may or may not be scored to assist in breaking it in half. Tablets however suffer from the disadvantage that they provide a fixed and inflexible dose of the steroid. While this may be quite acceptable or even desirable when treating adults it represents a considerable problem to the physician when treating children. Clearly in any population of children aged say under 10 there will be very considerable variations in body weight and thus very considerable variations in the amount of the steroid which it is desired to administer. With all drugs it is desirable not to administer an excessive dose, but when steroids, which can have growth retarding effects, are administered to growing children overdosing is particularly dangerous.

Liquid formulations of long acting steroids are known and orally administrated, but a large number of these comprise suspensions of the drug in the liquid vehicle, or are aqueous alcoholic solutions. Suspensions however suffer from the disadvantage that on storage and with the passage of time they tend to settle out and thus give a variable dosage when different levels in the container are used. Aqueous alcoholic solutions are particularly problematic when treating children or patients who either have adverse reactions to alcohol or who are taking drugs which react adversely with alcohol.

SUMMARY OF THE INVENTION

We have now found an improved steroid formulation which is suitable for oral administration, particularly to children, and which can be administered in a wide variety of easily variable doses. The formulation is also of intermediate duration of action (e.g. a biological half life to 12 to 24 hours), being quickly available to the gastrointestinal tract, and also avoids the use of ethanol, which is particularly objectionable in paediatric formulations. We have also found that stable formulations of relatively high concentration and high bioavailability can be made.

According to the invention therefore we provide an aqueous pharmaceutical solution comprising a steroid selected from prednisolone, prednisolone sodium phosphate, prednisone and methyl prednisolone, the steroid being present at a concentration of at least 0.3 mg/ml, the pH of the formulation being between 5 and 8 and the formulation containing a pharmaceutically acceptable preservative, a pharmaceutically acceptable chelating agent, and being substantially free of ethanol.

We prefer the formulation to contain at least 0.5 mg/ml, more preferably at least 0.7 mg/ml and especially at least 1.0 mg/ml of steroid. The concentration of steroid may be up to 5 mg/ml, but is preferably no more than 2 mg/ml, and may, in the case of prednisolone sodium phosphate, be about 1.3 mg/ml.

The composition may also contain a sweetening agent, e.g. an artificial sweetener such as aspartame, or a natural sweetener, e.g. a sugar such as sucrose or sorbitol. The presence of the sweetener and especially sorbitol, has been found to enhance the stability of the formulation. Furthermore, the presence of the sweetener helps to increase patient compliance in that it masks the unpleasant taste of the steroid. The importance of patient compliance cannot be overemphasised particularly with young children who are highly likely to reject unpalatable medicines. Sorbitol is preferred as the sweetener.

We prefer the formulation to contain 10 to 50, more preferably from 25 to 45, and desirably about 35, % w/w of the sugar, e.g. sorbitol. The sugar may comprise a mixture of sugars, e.g. sorbitol and sucrose.

The preservative may be any pharmaceutically acceptable preservative which is compatible with the formulation, e.g. sodium benzoate or an alkyl hydroxybenzoate such as propyl- or preferably methyl-hydroxybenzoate. We have found that methyl-hydroxybenzoate is advantageous in that, surprisingly, the composition is more stable on storage than when propyl-hydroxybenzoate is used. Clearly sufficient preservative should be present to maintain the solution in a sterile condition, and in general the solution contains up to about 0.1% w/w, e.g. from 0.01 to 0.08% w/w, of the preservative.

The pH of the solution is preferably in the range of 6.5 to 7.5.

We have found that the presence of a pharmaceutically acceptable chelating agent tends to enhance the stability of the formulation. A wide variety of chelating agents may be used, but we prefer to use an amino carboxylate compound, e.g. ethylene diamine tetraacetic acid or its salts, for example its disodium salt. The concentration of the chelating or sequestering agent may vary considerably, but in general we have found that a concentration of from about 0.01 to 0.1, preferably 0.02 to 0.05, % w/w is desirable.

The solution may also contain other excipients, diluents, carriers, buffering agents (e.g. phosphate buffers, such as sodium phosphate dibasic and/or sodium biphosphate, to maintain the desired pH), colouring agents, flavours, co-solvents, e.g. glycerol, etc, but we prefer to keep the amount of these ingredients to a minimum.

The solutions may be made up using standard pharmaceutical techniques.

The solutions of the invention are useful in the treatment of a variety of conditions. Particular conditions which may be mentioned are endocrine disorders, e.g. congenital adrenal hyperplasia, nonsuppurative thyroiditis and hypercalcemia associated with cancer; rheumatic disorders, e.g. psoriatic arthritis, rheumatoid arthritis, including juvenile rheumatoid arthritis, ankylosing spondylitis, acute and subacute bursitis, acute nonspecific tenosynovitis, acute gouty arthritis, post-traumatic osteoarthritis, synovitis of osteoarthritis and epicondylitis; collagen diseases; e.g. systemic lupus erythematosus, acute rheumatic carditis, mixed connective tissue syndrome, polymyositis, polymyalgia rheumatica, polyarteritis nodosa, Wegner's granulomatosis and systemic dermatomyositis (polymyositis); dermatologic diseases, e.g. pemphigus, bullous dermatitis herpetiformis, severe erythema multiforme (Stevens-Johnson syndrome), exfoliative dermatitis, mycosis fungoides, severe psoriasis and severe seborrheic dermatitis; allergic states, e.g. seasonal or perennial allergic rhinitis, bronchial asthma, contact dermatitis, atopic dermatitis, serum sickness, and drug hypersensitivity reactions; ophthalmic diseases, e.g. allergic conjunctivitis, keratitis, allergic corneal marginal ulcers, herpes zoster ophthalmicus, iritis and iridocyclitis, chorioretinitis, anterior segment inflammation, diffuse posterior uveitis and choroiditis, optic neuritis, and sympathetic ophthalmia; respiratory diseases, e.g. symptomatic sarcoidosis, Loeffler's syndrome, berylliosis, fulminating or disseminated pulmonary tuberculosis, and aspiration pneumonitis; hematologic disorders, e.g. idiopathic thrombocytopenic purpura, secondary thrombocytopenia, acquired (autoimmune) hemolytic anemia, erythroblastopenia (RBC anemia), and congenital (erythroid) hypoplastic anemia; neoplastic diseases, e.g. carcinoma of the breast, leukemias and lymphomas and acute leukemia; edematous states, e.g. to induce a diuresis or remission of proteinuria in the nephrotic syndrome, without uremia, of the idiopathic type or that due to lupus erythematosus; gastrointestinal diseases, e.g. ulcerative colitis and regional enteritis; hepatic disease, e.g. chronic active hepatitis, subacute hepatic necrosis, alcoholic cirrhosis in women; nervous diseases; e.g. acute exacerbations of multiple sclerosis and cerebral edema associated with neoplasms (especially metastatic); miscellaneous, e.g. tuberculous meningitis and subarachnoid block or impending block when used concurrently with appropriate antituberculous chemotherapy, trichinosis with neurologic or myocardial involvement and organ transplantation shock.

The solutions are particularly useful in the treatment of young children. The dosage used will vary with the age, size and response of the patient, with the particular steroid used, and with the condition to be treated. Thus, for example the initial dose may vary from 5 to 60 mg [measured as prednisolone base or its equivalent] (5–60 ml) per day depending on the specific disease entity being treated. In situations of less severity lower doses will generally suffice while in selected patients higher initial doses may be required. The initial dosage should be maintained or adjusted until a satisfactory response is noted.

We particularly prefer that the solution be used to treat the patient on alternate days.

The solution may be put up in suitable containers, e.g. bottles and the like containing 50 to 200, preferably about 120, ml of liquid, and the container may also be provided with a measuring device, e.g. a graduated beaker or spoon to facilitate ease and accuracy of dosage.

DESCRIPTION OF THE EMBODIMENTS

The invention is illustrated, but in no way limited by the following Example.

EXAMPLE

| Example Unit Dose (5 ml) | Ingredients | Quantity | |
|---|---|---|---|
| 2.182 ml | Sorbitol Solution, USP | 74.6 | l |
| 5.717 mg | Methylparaben, NF | 195.5 | g |
| 2.191 mg | Edetate, disodium, USP | 74.9 | g |
| 72.336 mg | Sodium phosphate, dibasic, USP | 2.474 | kg |
| 8.007 mg | Sodium biphosphate, USP | 273.6 | g |
| 5.000 mg | Prednisolone, sodium phosphate, USP (base) | 230 | g |
| 0.005 ml | Raspberry flavour, polak 500006U | 171 | ml |
| | Purified water, USP q.s ad | 171 | l |

Heat 6.8 liters (1.89 gallons) of purified water to about 95° C. and add 195.5 grams of methylparaben. Mix until completely dissolved and add this solution to the mixing tank, add the edetate disodium; add the sodium phosphate, dibasic, add the sodium biphosphate, add the prednisolone sodium phosphate, add the flavour. After 1-2 minutes, stop the mixer and add purified water to 760 liters and then mix until solution of all ingredients is accomplished. Bottle in 120 ml bottles.

We claim:

1. An aqueous pharmaceutical solution suitable for oral administration comprising as an active ingredient a steroid selected from the group consisting of prednisolone, prednisolone sodium phosphate, prednisone and methyl prednisolone, the steroid being present at a concentration of at least 0.3 mg/ml, the pH of the formulation being between 5 and 8 and the formulation containing a pharmaceutically acceptable preservative, a pharmaceutically acceptable chelating agent, and being substantially free of ethanol.

2. A solution according to claim 1 containing from 0.5 to 5 mg/ml of steroid.

3. A solution according to claim 2 containing from 0.7 to 2 mg/ml of steroid.

4. A solution according to claim 1 containing a sugar.

5. A solution according to claim 4 containing sorbitol or sucrose.

6. A solution according to claim 5 containing from 10 to 50% w/w of sugar.

7. A solution according to claim 6 containing from 25 to 45% w/w/ of the sugar.

8. A solution according to claim 1 containing methyl-hydroxybenzoate.

9. A solution according to claim 8 containing from 0.01 to 0.08% w/w of methyl-hydroxybenzoate.

10. A solution according to claim 1 having a pH in the range 6.5 to 7.5.

11. A solution according to claim 1 containing ethylene diamine tetraacetic acid or a salt thereof.

12. A solution according to claim 11 containing from 0.01 to 0.1% w/w of a salt of ethylene diamine tetraacetic acid.

13. A solution according to claim 12 containing from 0.02 to 0.05% w/w of the disodium salt of ethylene diamine tetraacetic acid.

14. A solution according to claim 1 containing a phosphate buffer.

15. A solution according to claim 1 containing prednisolone sodium phosphate in an amount of from 0.7 to 2 mg/ml, methyl-hydroxybenzoate in an amount of from 0.01 to 0.08% w/w, the disodium salt of ethylene diamine tetraacetic acid in an amount of from 0.02 to 0.05% w/w and sorbitol in an amount of from 25 to 45% w/w.

16. A method of treatment of a patient suffering from an endocrine disorder, a rheumatic disorder, a collagen disease, a dermatologic disease, an allergic state, an ophthalmic disease, a respiratory disease, a haematologic disorder, a neoplastic disease, an edematous state, a gastrointestinal disease or a nervous disease, which conprises administration of an effective amount of a solution according to claim 1 to the patient.

17. A method according to claim 16 wherein the patient is a child and from 5 to 60 ml of the solution is administered per 18. A method according to claim 16 wherein the biological half life of the solution is from 12 to 24 hours.

19. A solution according to claim 1 containing aspartame as a sweetening agent.

20. An aqueous pharmaceutical solution suitable for oral administration to a patient comprising:
(a) as an active ingredient a steroid selected from the group consisting of prednisolone, prednisolone sodium phosphate, prednisone and methyl prednisolone;
(b) methyl-hydroxybenzoate as a perservative in an amount of from about 0.01 to 0.08% w/w;
(c) ethylene diamine tetraacetic acid or a pharmaceutically acceptable salt thereof as a chelating agent in an amount of from about 0.01 to 0.2% w/w;
(d) sorbitol or sucrose as a sweetening agent in an amount of from about 10 to 50% w/w; and
(e) a phosphate buffer, the pH of the formulation being between about 6.5 and 7.5 and the solution being substantially free of ethanol.

* * * * *